United States Patent [19]
Hamada et al.

[11] Patent Number: 5,082,672
[45] Date of Patent: Jan. 21, 1992

[54] ENZYMATIC DEAMIDATION OF FOOD PROTEINS FOR IMPROVED FOOD USE

[75] Inventors: Jamel S. Hamada, Metairie; Wayne E. Marshall, Slidell, both of La.

[73] Assignee: The United States of American as represented by the Secretary of Agriculture, Washington, D.C.

[21] Appl. No.: 369,587

[22] Filed: Jun. 21, 1989

[51] Int. Cl.$^5$ ............................................. A23L 1/00
[52] U.S. Cl. ............................................. 426/7; 426/46; 426/52; 426/63; 426/42; 426/656; 426/657
[58] Field of Search ............... 426/7, 46, 52, 63, 656, 426/42, 656

[56] References Cited

U.S. PATENT DOCUMENTS

| | | | |
|---|---|---|---|
| 4,302,473 | 11/1981 | Mikami et al. | 426/46 |
| 4,757,007 | 7/1988 | Satoh et al. | 426/46 |

FOREIGN PATENT DOCUMENTS

| | | | |
|---|---|---|---|
| 0201247 | 7/1983 | Fed. Rep. of Germany | 426/46 |
| 4925346 | 6/1974 | Japan | 426/46 |

OTHER PUBLICATIONS

Hamada et al., J. Food Sci., vol. 53, No. 2 (1988), pp. 671-672.
Hamada et al., J. Food Sci., vol. 53, No. 4 (1988), pp. 1132-1149.

*Primary Examiner*—Marianne Cintins
*Attorney, Agent, or Firm*—M. Howard Silverstein; John D. Fado; Joseph A. Lipovsky

[57] ABSTRACT

Deamidation of food proteins by *Bacillus circulans* peptidoglutaminase was impaired by the large molecular size and unique conformation of these proteins. The limited ability of peptidoglutaminase to deamidate food proteins was increased dramatically by protein hydrolysis and altering protein conformation, principally by moist heat. A method to prepare enzymatically deamidated food proteins with a wide range of protein deamidation was developed. Enzymatic deamidation of proteins improved their functional properties especially in the mild acidic pH region (e.g., 4-6).

5 Claims, 10 Drawing Sheets

Figure 10 ns under mildly acidic conditions. Improving solubility, emulsifying or foaming properties of edible proteins enhance their use as functional ingredients in many food systems, including beverages, pourable and nonpourable dressings, whipped toppings, frozen desserts, confections, baked goods and meat.

ENZYMATIC DEAMIDATION OF FOOD PROTEINS FOR IMPROVED FOOD USE

BACKGROUND OF THE INVENTION

1. Field of the Invention

The functional properties of food proteins depend on their conformation in food systems. The relationship of protein structure to functionality is such that altering the chemistry of food proteins can improve functional properties such as solubility, viscosity, gelation, fat emulsification and foaming. The conversion of protein amide groups to carboxyl groups by deamidation improves solubility and other physical properties of proteins under mildly acidic conditions. Improving solubility, emulsifying or foaming properties of edible proteins enhance their use as functional ingredients in many food systems, including beverages, pourable and nonpourable dressings, whipped toppings, frozen desserts, confections, baked goods and meat.

An enzymatic approach to protein deamidation offers several advantages over a chemical approach, including the speed of reaction, the fact that the reactions take place under mild conditions such as neutral pH and room temperature and, most importantly, they are highly specific. The mild conditions reduce energy costs and the high specificity increases processing efficiency and minimize the need for downstream processing.

2. Description of the Prior Art

Enzymatic deamidation of food proteins has received little attention until recently. Gill et al., Irish J. Food Sci. Technol., vol. 9, (1985), p. 33, detected limited deamidating activity of *Bacillus circulans* peptidoglutaminase towards casein and whey protein hydrolysate. Motoki et al., Agric. Biol. Chem., vol. 50, (1986), p. 3025, used guinea pig transglutaminase to catalyze the hydrolysis of amide groups of glutamine residues in casein. Kato et al., J. Agric. Food Chem., vol. 35, (1987), p. 224, developed a method to deamidate food proteins by treatment with proteases at pH 10. They observed, however, a significant amount of uncontrolled proteolysis concurring with deamidation. Furthermore, processing of food proteins at pH 10 is undesirable for a variety of reasons including the implication of alkali-treated foods in causing kidney damage in rats [Woodard and Short, J. Nutr., vol. 103, (1973), p. 569].

Hamada et al., J. Food Sci., vol. 53, (1988), p. 671, used the peptidoglutaminase from *B. circulans* to deamidate soy peptides and proteins. Peptidoglutaminase (referred to as PGase also) readily deamidated soy peptides but its activity towards the intact protein was small. They suggested that limited deamidation was due to the large molecular size and/or unique conformation of soy protein. There is a need to provide for an efficient enzymatic deamidation process for food proteins of large molecular size and unique conformation at near physiological pH.

SUMMARY OF THE INVENTION

The objective of this inventio is to alter protein molecular size by proteolysis or the modification of protein conformation, principally by heat treatment in order to enhance protein deamidation using peptidoglutaminase.

Heat treatment and/or proteolysis of proteins significantly increased the degree to which they could be deamidated by peptidoglutaminase purified from *Bacillus circulans*. With heat treatment and proteolysis of soy protein to a degree hydrolysis (DH) value of 20%, over 27% protein deamidation could be achieved. Although the presence of various salts and disulfide reducing agents had little effect on soy protein deamidation, they could be a major factor enhancing the deamidation of other protein, e.g., wheat gluten. A wide range of protein deamidation can be achieved by heat or proteolysis alone or a combination of both, which, the deamidation process, allows the production of food proteins with different degrees of deamidation having improved functionality to be used in a wide variety of food applications. A method for the preparation of peptidoglutaminase-modified food proteins with up to 60% deamidation is described.

BRIEF DESCRIPTION OF THE DRAWINGS

FIG. 7A–FIG. 7D—Solubility of native and modified soy proteins at pH values 2-9: A) Water extract of soy flakes; B) 2 DH heated 15 min: Control (○), 6% deamidated (■) or 30 min: Control (●), 8.2% deamidated (▲); C) 4 DH heated 15 min: Control (○), 12.8% deamidated (■) or 30 min: Control (●), 16.0% deamidated (▲).

FIG. 8A–FIG. 8D—Emulsifying activity of native and modified soy proteins at pH values 2-9: A) Water extract of soy flakes; B) 2 DH heated 15 min: Control (○), 6% deamidated (■) or 30 min: Control (●), 8.2% deamidated (▲); C) 4 DH heated 15 min: Control (○), 12.8% deamidated (■), or 30 min: Control (●), 16.0% deamidated (▲).

FIG. 9A–FIG. 9D—Emulsion stability of native and modified soy proteins: A) water extract of soy flakes; B) 2 DH heated 15 min: Control (○), 6% deamidated (■) or 30 min: Control (●), 8.2% deamidated (▲); C) 4 DH heated 15 min: Control (○), 12.8% deamidated (■) or 30 min: Control (●), 16.0% deamidated (▲).

DETAILED DESCRIPTION OF THE INVENTION

Enhancement of Peptidoglutaminase Deamidation of Soy Proteins

EXAMPLE 1

Materials

CBZ-L-glutamine was purchased from Sigma Chemical Co., St. Louis, Mo. and t-BOC-L-glutaminyl-L-proline from Peptides International, Louisville, Ky. Nutrisoy 7B flakes were obtained from Archer Daniels Midland Co., Decatur, Ill. Alcalase 2.4 L (2.4 Anson units/g) was obtained from Novo Laboratories Inc., Wilton, Conn. *Bacillus circulans* culture (ATCC

21590) was obtained from the American Type Culture Collection, Rockville, Md. Other chemicals were reagent grade or the highest purity obtainable.

EXAMPLE 2

Preparation of Soy Protein Substrate

Soy protein, used as substrate for peptidoglutaminase deamidation and as starting material for the proteolysis experiments, was a water extract of soy flakes. Nutrisoy 7B flakes were extracted with water (1:20 ratio) at 25° C. for 1 hour (hr) and passed through 16 layers of cheesecloth to remove insoluble materials. The freeze-dried preparation was 55.0% protein.

EXAMPLE 3

Preparation of Peptidoglutaminase

Phosphate gel eluate was prepared from crude extract according to Hamada et al. (1988) Ibid., incorporated herein by reference. Bacillus circulans (ATCC #21590) cells were grown and harvested according to Kikuchi et al., Biochem., vol. 10, (1971), p. 1222 and Kikuchi and Sakaguchi, Methods in Enzymol., vol. 45, (1976), p. 485. The microorganism was grown in a 20 L VirTis "43" series Fermentor (VirTis Co., Gardiner, N.Y.) containing 8.5 L medium, at 30° C. for 17-20 hr with aeration (8.5 L air per min) and 150 rpm stirring. The cells were concentrated using an ultrafiltration unit (Model DC 10 LA lab scale Amicon cartridge, Amicon Corp., Danvers, Mass.) then centrifuged. The cell pellet was suspended in 0.01M phosphate buffer, pH 8.0, and ruptured by a 2 minute (min) sonication in an ice bath (Cell Disruptor model W375, Heat Systems-Ultrasonics, Inc., Plainview, N.Y.) and a 3 min homogenization at 16,000 rpm using an Omni Mixer (Ivan Sorvall Inc., Norwalk, Conn.). Cellular debris was removed by centrifugation. The supernatant was dialyzed against 0.005M phosphate buffer, pH 7.2 for 24 hr. Alumina Cγ and calcium phosphate gels were used to fractionate the enzyme by adsorption according to the method of Bach et al., Biochem. J., vol. 40, (1946), p. 229. The eluate contained 35.5% protein, was lyophylized and stored at −5° C. until needed.

EXAMPLE 4

Protein Determination

The protein content of PGase was determined by the method of Lowry et al., J. Biol. Chem., vol. 193, (1951), p. 265, using bovine serum albumin as the standard. The protein content of soy protein was determined by the Kjeldahl method using 6.25 as a conversion factor.

EXAMPLE 5

Peptidoglutaminase Assay and Measurement of Deamidation

A 1 mL aliquot of the enzyme solution containing 2 mg of freeze-dried phosphate gel eluate as obtained from Example 3 was added to 2 mL of substrate in 0.05M phosphate buffer, pH 7.5. The substrate concentrations were 0.25% CBZ-L-glutamine to assay peptidoglutaminase I, 0.10% t-BOC-L-glutaminyl-L-proline to assay peptidoglutaminase II and 5% soy protein or soy protein hydrolysate to study soy protein deamidation by peptidoglutaminase. Substrate concentrations were determined to be sufficient for saturation of the enzyme. Reaction mixtures were incubated at 30° C. for 1 hr, and 0.3 mL of 50% TCA was added to stop the reaction. The ammonia content of the reaction mixtures and controls was measured with an Orion ammonia electrode (model 95-10) connected to an Ion Analyzer model EA 940 (Orion Research Inc., Cambridge, Mass.). The extent of deamidation was calculated as the ratio of ammonia released enzymatically to the ammonia released by the soy protein after amide hydrolysis with 2N HCl at 100° C. for 4 hr [Wilcox, Methods in Enzymol., vol. 11, (1967), p. 63].

EXAMPLE 6

Protein Hydrolysis

The pH of the dispersions of both undenatured and heat-treated soy proteins (4 g in 100 mL water) was adjusted to 8.0 and then 0.05 g Alcalase 2.4 L was added to start the proteolysis. The extent of protein hydrolysis was controlled quantitatively using the pH-stat method of Adler-Nissen, Enzymatic Hydrolysis of Food Proteins, Elsevier Applied Science Publishers, (1986), London and New York. During hydrolysis at 50° C., the reaction mixture was continuously titrated to pH 8.0 with 0.5N NaOH using an Auto Titrator (Radiometer A/S, Copenhagen). Depending on the degree of hydrolysis desired, the reaction mixture consumed 0.2 to 8.3 mL 0.5N NaOH. Proteolysis was stopped by a 10 min heat treatment at 85° C. Hydrolysates were freeze-dried. The degree of hydrolysis, or percent of peptide bonds cleaved, was determined by reacting free amino groups with trinitrobenzenesulfonic acid [Alder-Nissen, J. Agric. Food Chem., vol. 27, (1979), p. 1258].

EXAMPLE 7

Protein Treatment with Heat, Salt or Disulfide Reducing Agents

Heat treatments were carried out using 5% dispersions of soy protein or soy protein hydrolysate in 0.05M phosphate buffer, pH 7.5. A 2 mL protein suspension in culture tubes was covered with screw caps, placed in a boiling water bath and heated for 10–120 min at 100° C. Concentration of salts and reducing agents were based on 3 mL total volume of reaction mixture. Salt or reducing agent was dissolved in 0.5 mL water, added to 2 mL hydrolysate or protein dispersion, and the mixture was stirred for 15 min. Peptidoglutaminase (2 mg eluate dissolved in 0.5 mL water) was added to start the reaction.

Susceptibility of Heat-Treated Soy Protein to PGase Deamidation

Figure 1:
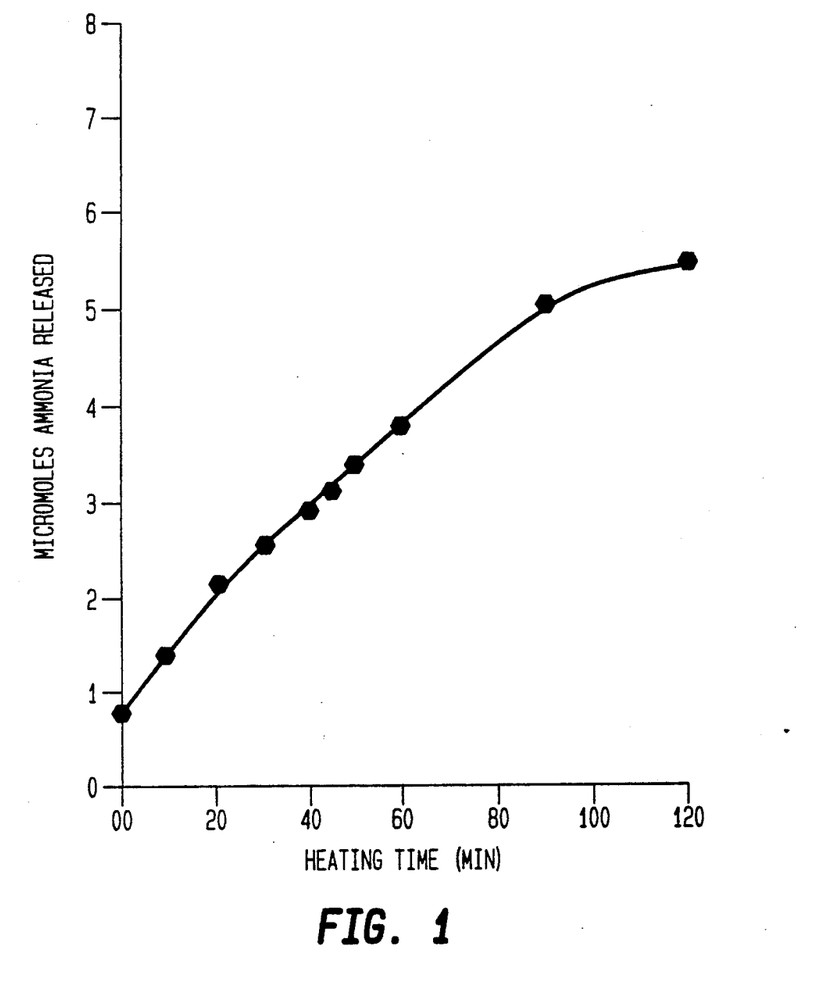
FIG. 1—Effect of heat treatment of soy protein on PGase deamidation.

The ability of peptidoglutaminase to deamidate the intact soy protein was limited (less than 1.5% deamidation) due to the large molecular size and/or unique conformation of soy protein. FIG. 1 presents the effect of soy protein heating time on protein deamidation by PGase. Heating soy protein at 100° C. for 2 hr increased deamidation 5.5-fold. When soy protein was heated at intervals from 0 to 90 min before deamidation, the subsequent extent of deamidation increased in an almost linear manner before leveling off.

Figure 2:
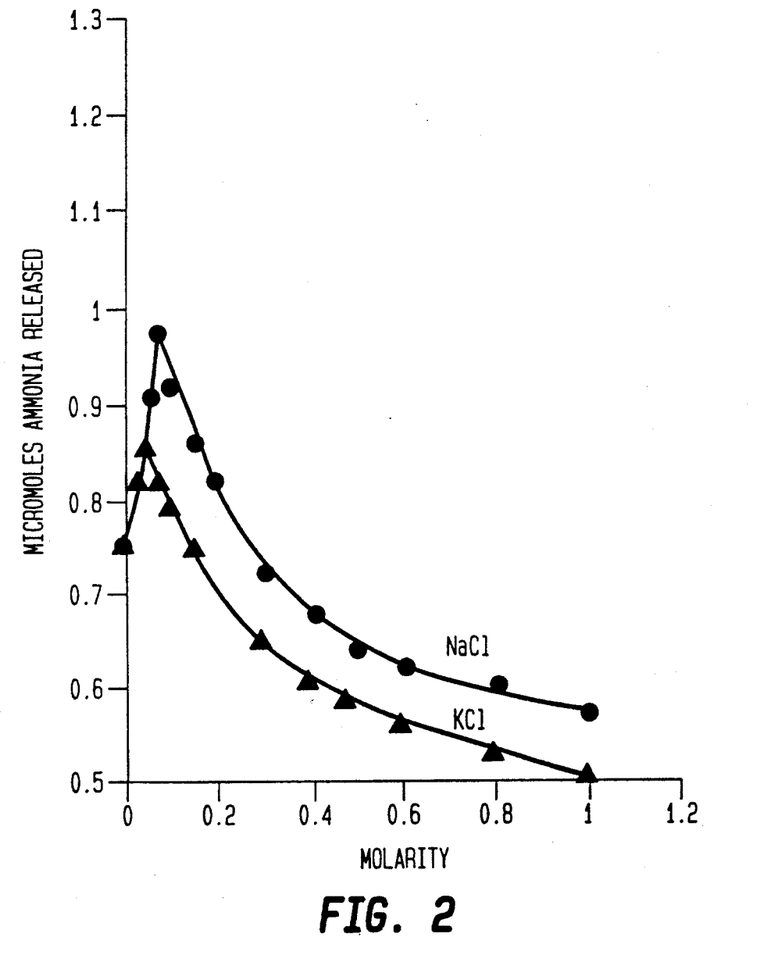
FIG. 2—Effect of NaCl and KCl concentrations on PGase deamidation of soy protein.

Influence of Salt and Disulfide Reducing Agents on Soy Protein and Its Subsequent Deamidation by PGase The ability of PGase to deamidate soy protein can be increased slightly with the addition of less than 0.1M sodium chloride and 0.05M potassium chloride as shown in FIG. 2. This should be taken into account in determining the amount of salt used to prepare the protein for deamidation, since NaCl is commonly used to adjust the ionic strength of enzyme reaction mixtures.

Addition of 0.001 or 0.005M cysteine or 0.002 or 0.01M sodium sulfite, two reducing agents commonly used in foods, to reaction mixtures had no effect on the deamidation of the protein substrate by PGase. However, a 6-10% improvement in deamidation was observed when 0.001M cysteine and heat treatment were used with proteins hydrolyzed to approximately 2-5% DH. Cysteine and sodium sulfite have been used at comparable concentrations to break disulfide bonds in food proteins, including soy protein [Circle et al., Cereal Chem., vol. 41, (1964), p. 157]. Breaking disulfide bonds in soy protein did not render the protein more susceptible to PGase attack. However, disulfide breaking agents can increase extractability and solubility of other proteins such as wheat proteins [Wren and Nutt, J. Sci. Fd Agric., vol. 18, (1967), p. 119], and enhance the peptidoglutaminase deamidation of these proteins accordingly.

Proteolysis of Soy Protein and Its Effect on PGase Activity

Proteolysis is a convenient way to reduce the molecular size of proteins by reducing the length of the amino acid chains. When soy proteins were hydrolyzed by Alcalase before deamidation, the extent of deamidation increased linearly to 10% DH and rapidly leveled off (FIG. 3A). From 0 to 20% DH, an 8-fold increase in deamidation was observed. After about 10% of the total peptide bonds were cleaved, new peptide conformations offer maximum accessibility of amide groups to PGase, providing a leveling off in the quantity of deamidation that could occur.

Effect of Heat Treatment and Proteolysis on PGase Deamidation of Soy Protein

Figure 3:
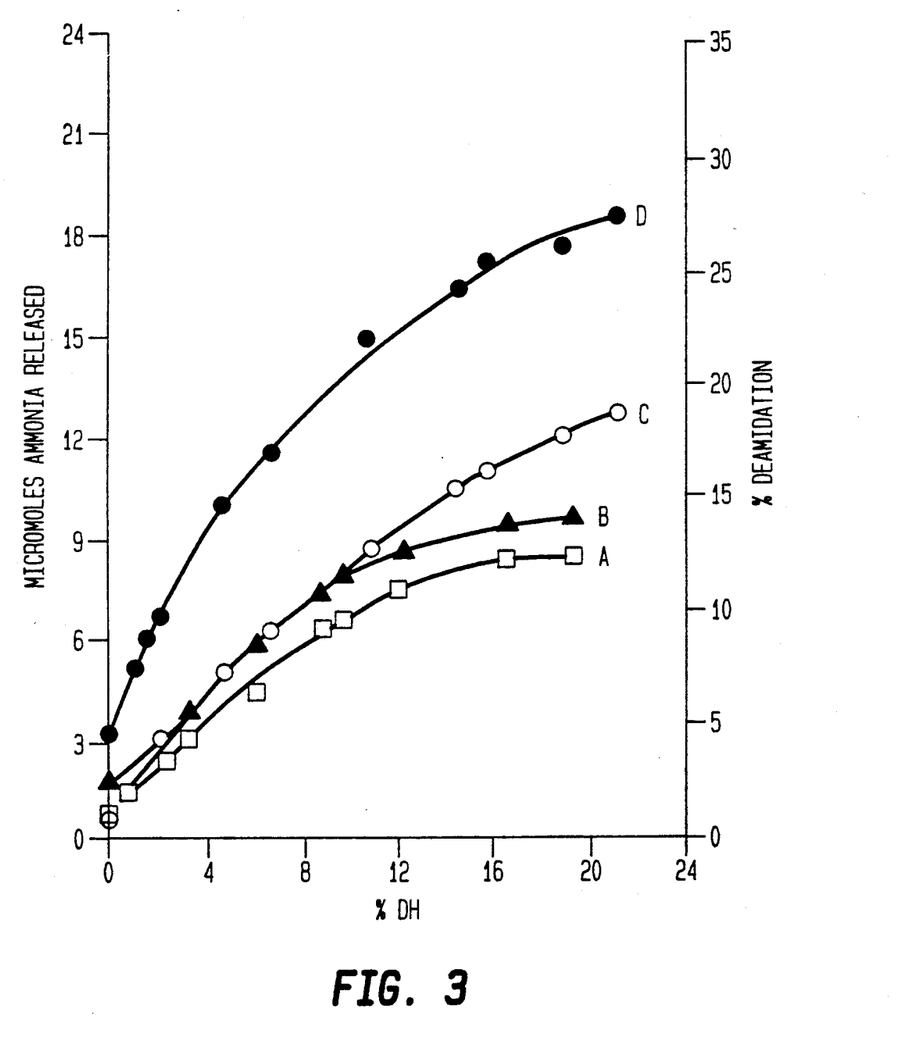
FIG. 3—Effect of Alcalase proteolysis and heat treatment on the PGase deamidation of soy protein: (A) unheated, (B) heated after proteolysis, (C) heated before proteolysis, and (D) heated before and after proteolysis.

Heating soy protein at 100° C. for 15 min after Alcalase hydrolysis increased the rate of deamidation as a function of DH at all degrees of hydrolysis (compare FIG. 3A to FIG. 3B). When soy protein was heated at 100° C. for 15 min prior to hydrolysis (FIG. 3C), the degree of deamidation was similar to the post-heat treatment results (FIG. 3B) at DH values below 10% but deamidation was greater at DH values above 10%. Pre- and post-heat treatment of hydrolyzed soy protein produced the greatest degree of deamidation (FIG. 3D) at all DH values. As a result of the two heat treatments, deamidation of soy protein increased more than 27-fold when compared to the deamidation of soy protein with no heat treatment and no proteolysis. Results presented in FIG. 3 illustrate that heat treatment improves soy protein susceptibility to deamidation. Heat treatment caused the protein or polypeptide to unfold and the new conformations were apparently more susceptible to PGase activity. Since heat treatment improved deamidation, even for hydrolysates with relatively larger DH values, a portion of the polypeptide chain might still retain some secondary and tertiary structure. Evidently, this residual structure must be disrupted before glutamine residues become completely accessible to PGase. Accordingly, it may be possible to estimate the amount of secondary and tertiary structure in a soy polypeptide using heat treatment and PGase. The results presented here differ form observations of Gill et al. (1985), Ibid. They found little PGase deamidation of whey and casein proteins even after protein hydrolysis. Also, when heat and other protein-denaturing conditions were used, PGase deamidation was not observed for these proteins.

Combining Protein Substrate Treatments for PGase Deamidation

Table 1 presents the effect of combining heat treatment, salt, reducing agent and enzyme concentration at various degrees of soy protein hydrolysis on the deamidation of soy protein. Reaction mixtures were incubated at 30° C. for 120 min to maximize deamidation. Doubling the concentration of enzyme in the reaction mixture had little effect on soy protein deamidation.

TABLE 1

Deamidating Activity of Peptidoglutaminase Towards Untreated, Heat-treated, or Proteolyzed Soy Protein

| | Micromoles ammonia released in reaction mixture[a] | | | |
|---|---|---|---|---|
| | 2 mg PGase | | 4 mg PGase | |
| Sample % DH | Untreated | Treated[b] | Untreated | Treated[b] |
| 0 | 1.0 | 2.9 | 1.0 | 3.0 |
| 1.4 | 2.0 | 4.5 | 2.2 | 4.7 |
| 4.8 | 4.7 | 8.5 | 5.4 | 9.5 |
| 6.7 | 6.3 | 9.5 | 7.5 | 10.8 |

[a]Reaction mixture contained 0.1 g preheated protein (100° C. 15 min) and 2 or 4 mg PGase; incubated at 30° C. for 2 hr.
[b]Soy protein was modified by heating for 30 min at 100° C. in 0.05M phosphate buffer, pH 7.5 with 0.05M phosphate buffer, pH 7.5 with 0.001M cysteine and 0.1M NaCl.

In Table 1, only low levels of proteolysis were selected. Enzymatic hydrolysis of soy proteins is usually accompanied by bitter taste. Low levels of bitterness can be obtained by restricting the degree of hydrolysis to small levels (3-5% [Adler-Nissen (1986) Ibid.]. At DH values of 3.5%, 10-15% of soy protein deamidation by PGase can be achieved (FIG. 3). This respectable level of deamidation should be sufficient to observe changes in the solubility and physical properties of the deamidated proteins. Furthermore, glutamate-containing peptides are thought to mask the bitterness released at larger DH values (Adler-Nissen, (1986), Ibid. Accordingly, combining deamidation with proteolysis may allow hydrolysates with larger degrees of hydrolysis before bitterness is a problem.

Modification of Food Proteins by Peptidoglutaminase

EXAMPLE 8

Materials

Egg albumin, corn gluten meal, wheat gluten and enzymatically hydrolyzed corn gluten and soy proteins (Peptone type IV) were purchased from Sigma Chemical Co. (St. Louis, Mo.). Enzymatic protein hydrolysates from casein, lactalbumin, egg albumin, soy (papaic) and rice were obtained form Deltown Chemurgic Co. (Fraser, N.Y.).

EXAMPLE 9

Optimizing PGase Reaction

The best reaction conditions for the peptidoglutaminase deamidation of food proteins were determined. Studies were carried out using Peptone IV in 0.05M sodium phosphate buffer, pH 7.5 as the substrate, and crude extract preparation of peptidoglutaminase. The suitable amount of substrate needed to saturate the enzyme and the incubation time at 30° C., required to complete the deamidation reaction were determined.

EXAMPLE 10

Procedure for the Peptidoglutamina Deamidation of Food Proteins

Figure 6:
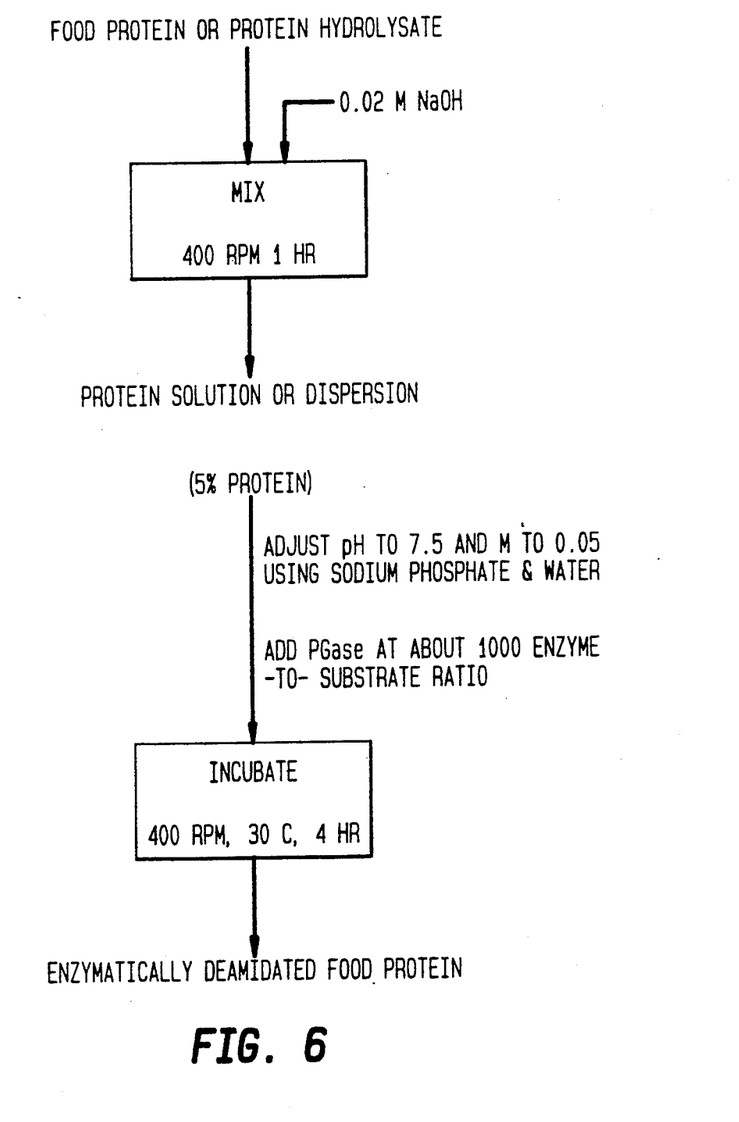
FIG. 6—Process for making peptidoglutaminase-modified food proteins.

Protein or protein hydrolysate was solubilized in dilute NaOH to about 5% total protein (N×nitrogen factor). Ten milliter of 0.02M NaOH was added to 0.5-3.0 g of the protein or protein hydrolysate, depending on sample nitrogen content, and the dispersion or slurry was stirred at 400 rpm at 25° C. for 1 hr. The pH of the solution was 11.2. Eight milliliter of mon- and di-hydrogen sodium phosphate solutions and water were added to adjust the pH to 7.5 and the buffer molarity to 0.05. Two milliter of PGase crude extract containing 0.5 mg protein was added to the substrate. Reaction mixture was incubated at 30° C. for 4 hr with 400 rpm stirring. A flow chart summarizing this method for the preparation of deamidated proteins, is given in FIG. 6.

Enzymatic Protein Hydrolysis and Deamidation

Table 2 presents the results on the analysis of nitrogen, free ammonia and total amide content of food proteins. Proteins, either prepared in this laboratory or obtained from commercial sources, contained insignificant amounts of free ammonia (0.017-0.032 millimoles per gram protein). Also there was no significant deamidation occurred during the preparation of soy protein hydrolysates using alcalase, heat treatment or combination of both. Relatively small amounts of ammonia were released from soy protein during alcalase hydrolysis under conditions given in FIG. 3.

Ammonia concentration ranged from 0.002 to 0.03 millimoles ammonia per gram protein and was proportional to DH (degree of hydrolysis) values. On the other hand, some of the commercial protein hydrolysates contained considerable amount of free ammonia, which is an indication of protein deamidation occurred during its enzymatic proteolysis. Kato et al. (1987), Ibid., reported that the extent of deamidation with proteolytic enzymes was dependent mainly on the type of protease used as well as the pH and temperature of the reaction. Free ammonia concentration ranged form 0.032 to 0.250 millimoles ammonia/g protein in commercial protein hydrolysates. Considering the total amide content in these hydrolysates (Table 2) these levels of ammonia were equivalent to from 0.5 to 29.4% of the total amide in the protein hydrolysate. The smallest levels of deamidation were observed with soy protein and egg albumin hydrolysates (0.5-2.5%), and the greatest levels were observed with two casein protein hydrolysates (17.2 and 29.4), but the rest of the food protein hydrolysates averaged 9.9% with a range of 8.6-11.5% deamidation.

Extensive PGase Deamidation of Food Proteins Optimizing the PGase Reaction

Figure 4:
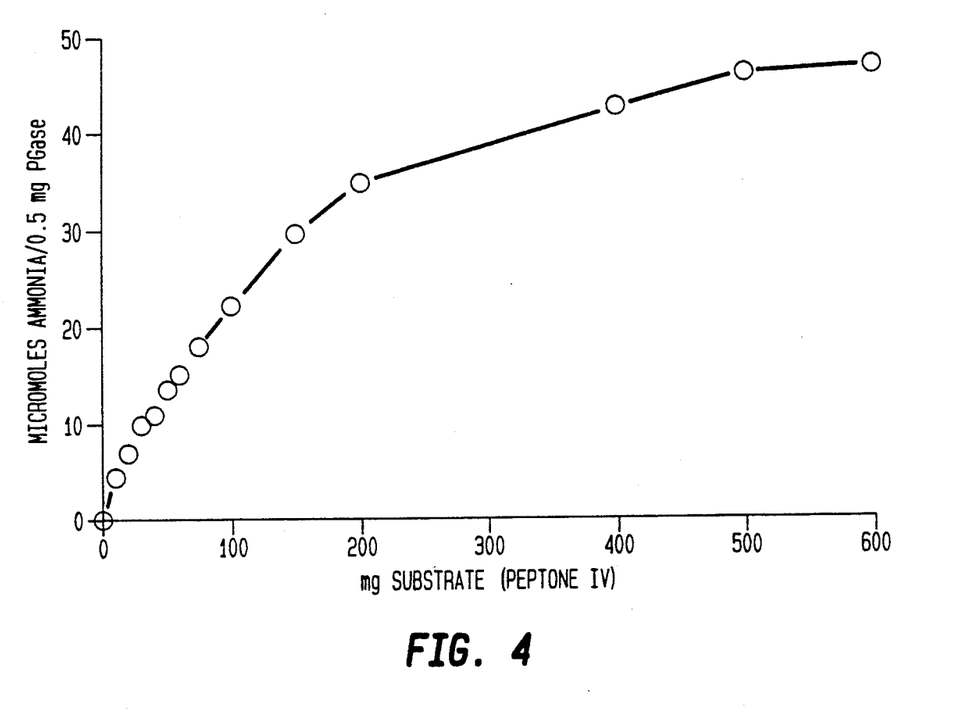
FIG. 4—Saturation of peptidoglutaminase by Peptone IV substrate.
Figure 5:
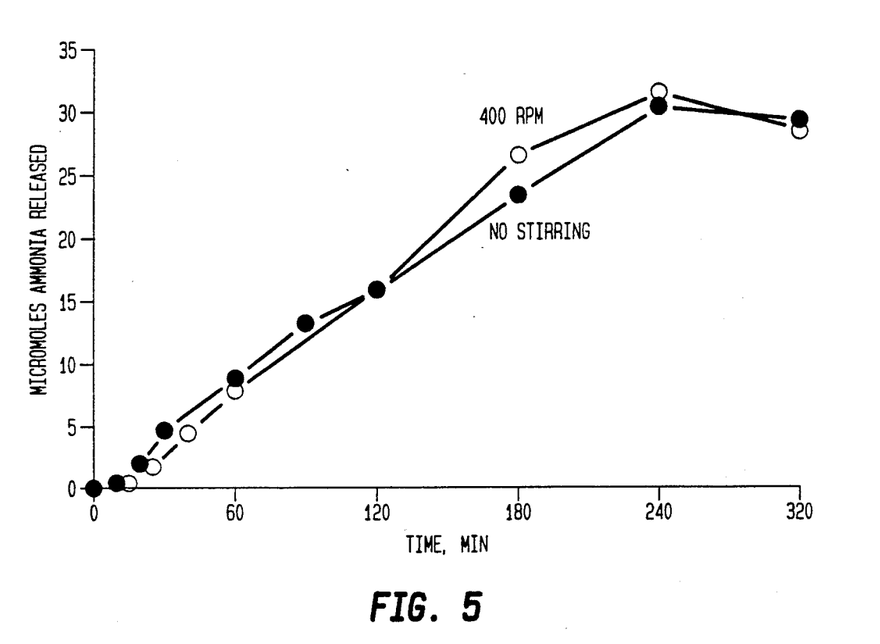
FIG. 5—Progress of peptidoglutaminase deamidation of Peptone IV as a function of time.

In all previous examples, the methods described were intended to study the effects of certain variable (e.g., heat treatment, proteolysis ... etc) on the specific activity of peptidoglutaminase. Specific activity is an experimental measurement of the enzyme ability to catalyze the deamidation reaction in a unit of time (e.g., an hour) per unit weight of the enzyme preparation under set experimental conditions. Industrially, the maximum degree of deamidation is required, which can often take a considerably longer time to execute at an economical enzyme dose. To attain this goal, the amount of protein substrate required for the enzyme saturation was first determined using Peptone type IV as substrate. FIG. 4 presents levels of Peptone IV required for the saturation of 0.5 mg peptidoglutaminase. It appears that a substrate-to-enzyme ratio of 1,200 is sufficient for the enzyme saturation with the substrate. Table 3 gives the progress of peptidoglutaminase deamidation of soy protein hydrolysate at various substrate-to-enzyme ratios, as a function of time. The greater the substrate-to-enzyme ratio, the longer the time required to complete the deamidation reaction. Data in both Table 3 and FIG. 5 also revealed that the reaction was complete after 4 hr at a substrate-to-enzyme ratio 2.5 times lower than that of saturation level. Accordingly, reaction mixtures were incubated at 30° C. for 4 hr to maximize deamidation. It should be noted that although stirring of the reaction mixture of peptone IV and PGase during incubation was unnecessary (FIG. 5), many other food protein hydrolysates especially corn protein hydrolysate needed 400 rpm stirring to enhance the deamidation of these proteins.

Procedure for the PGase Deamidation of Food Proteins

The present invention provides methodology for treating food proteins with peptidoglutaminase to obtain enzymatically deamidated products with a broad spectrum of the extent of deamidation to be used in a wide variety of food applications. The first part of the

TABLE 2

Protein, Free Ammonia, Total Amide and Peptidoglutaminase Deamidation of Food Proteins and Protein Hydrolysate

| Protein or Protein Hydrolysate | % N | Nitrogen Factor | % Protein* | Free Ammonia Millimole per g Protein | Total Amide Millimole per g Protein | % Proteolysis Deamidation** | % PGase Deamidation |
|---|---|---|---|---|---|---|---|
| Water Extract of Soy Flakes | 9.1 | 6.25 | 56.9 | 0.026 | 1.08 | 0.0 | 6.4 |
| Soy Peptone type IV | 9.3 | 6.25 | 58.5 | 0.032 | 0.68 | 0.5 | 56.0 |
| Papaic Soy Hydrolysate | 12.9 | 6.25 | 80.6 | 0.036 | 0.90 | 1.0 | 14.5 |
| Wheat Gluten | 12.8 | 5.70 | 73.0 | 0.018 | 2.50 | 0.0 | 1.3 |
| Corn Gluten | 10.1 | 5.60 | 56.6 | 0.032 | 1.23 | 0.0 | 2.8 |
| Corn Gluten Hydrolysate | 9.8 | 5.60 | 54.9 | 0.174 | 1.22 | 9.1 | 30.9 |
| Rice Protein Hydrolysate | 1.4 | 5.95 | 8.3 | 0.163 | 1.38 | 9.1 | 13.7 |
| Egg Albumin | 13.2 | 6.25 | 82.5 | 0.017 | 0.86 | 0.0 | 0.0 |
| Papaic Egg Albumin Hydrolysate | 12.2 | 6.25 | 76.3 | 0.036 | 0.65 | 2.9 | 39.6 |
| Lactalbumin Hydrolysate, lot A | 12.3 | 6.38 | 78.5 | 0.121 | 0.71 | 11.2 | 39.0 |
| Lactalbumin Hydrolysate, lot K | 9.7 | 6.38 | 61.9 | 0.146 | 0.85 | 11.5 | 37.4 |
| Pancreatinic Casein Hydrolysate | 12.5 | 6.38 | 79.8 | 0.099 | 0.88 | 8.6 | 30.4 |
| Casein Hydrolysate, lot L | 11.1 | 6.38 | 70.8 | 0.249 | 1.12 | 17.2 | 27.2 |
| Casein Hydrolysate, lot N | 12.4 | 6.38 | 79.1 | 0.450 | 0.95 | 29.4 | 26.3 |

*% Protein = % N × Nitrogen Factor
**Calculated from free ammonia and total amide contents invention, however, was described in terms of the treatment of soy proteins. It should be pointed that this invention is not intended to be limited to only soy protein. A method was developed to produce several food proteins with significant degrees of deamidation (See Example 10). Many proteins, especially plant seed storage proteins, and even their partially hydrolyzed protein products are generally not quite soluble in aqueous solutions.

TABLE 3

Progress of Peptidoglutaminase Deamidation of Soy Peptone as a function of time

| Substrate-to-Enzyme Ratio | Percent of Total Amides Hydrolyzed by PGase | | |
|---|---|---|---|
| | 1 hr | 2 hr | 4 hr |
| 3000 | 6.4 | 10.5 | 14.9 |
| 1200 | 14.7 | 20.0 | 34.5 |
| 300 | 25.9 | 31.6 | 56.4 |

As the pH is changed from the isoelectric point to more acidic or alkaline values, the protein or the protein hydrolysate becomes relatively soluble or quite dispersible. Dilute sodium hydroxide solution was used to obtain soluble substrate, that were suitable for PGase deamidation. Table 2 gives the percent of PGase deamidation of food proteins, using the method described in Example 10. As would be expected, peptidoglutaminase failed to deamidate egg albumin because of the egg protein lacked solubility at pH 7-8. However, the enzyme readily deamidated the egg albumin hydrolysate. Once again these data demonstrate the importance of protein hydrolysis in rendering the protein substrate more accessible to peptidoglutaminase attack. Accordingly, proteolysis, moist heat or a combination of both treatments are necessary to render any food protein susceptible to PGase attack and must be used as a pretreatment prior to PGase reaction. The peptidoglutaminase deamidation of hydrolysates was extensive, even for protein hydrolysates such as casein hydrolysate, which was deamidated extensively prior to peptidoglutaminase treatment.

Functionality of Enzymatically Deamidated Proteins

EXAMPLE 11

Preparation of Soy Protein Substrate and PGase Deamidation

Figure 10:
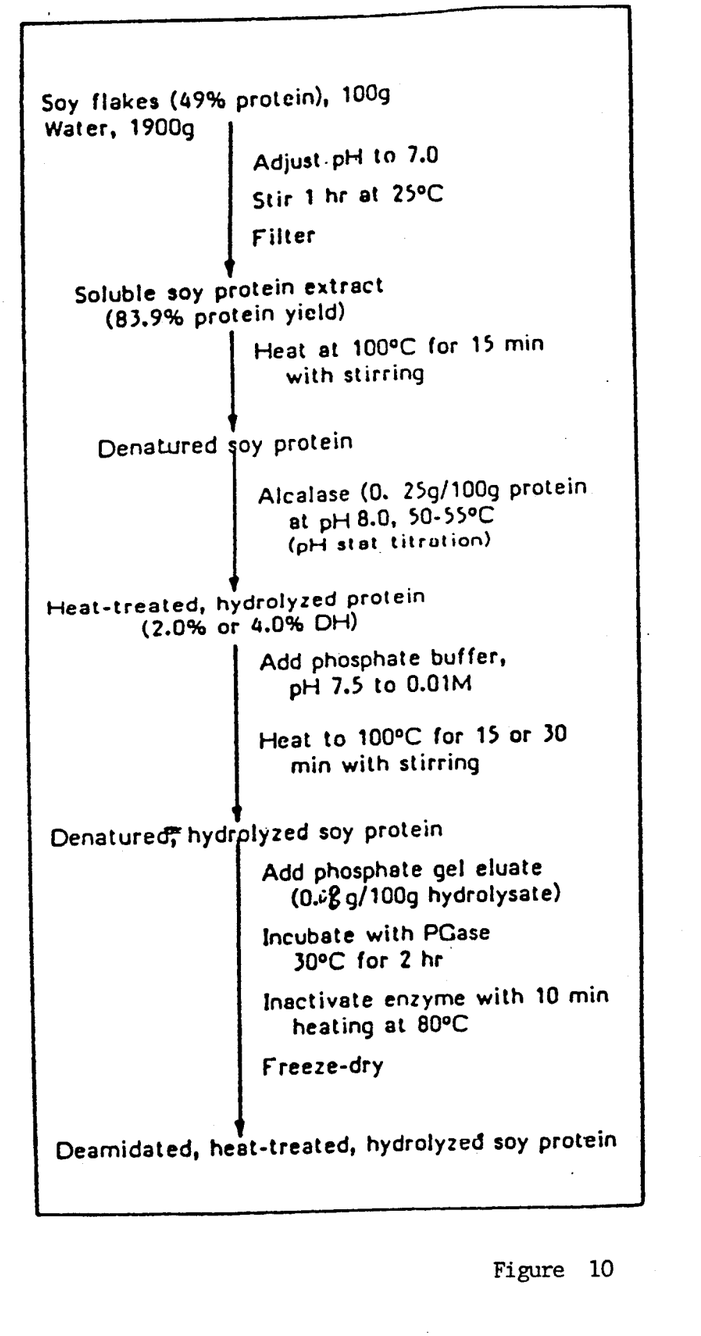
FIG. 10—Shows a flow chart summarizing the preparation of enzymatically deamidated soy proteins.

A flow chart summarizing the preparation of hydrolysed, deamidated soy protein is given in FIG. 10. Soy flakes were extracted with water at 25° C. for 1 hr, then filtered. The soy protein filtrate was heated at 100° C. for 15 min, cooled to 50° C., the pH adjusted to 8.0 and Alcalase 2.4 L added to start proteolysis. The extent of hydrolysis was controlled to 2.0 or 4.0 DH by the pH-stat method (Novo Industri A/S, 1978), using an Auto Titrator (Radiometer A/S, Copenhagen). Both the 2.0 and 4.0 DH hydrolysates were divided into two parts. One-half of the hydrolysate was heated to 100° C. for 15 min, while the other half was heated to 100° C. for 30 min. Each of the heat-treated hydrolysates were deamidated with PGase from the phosphate gel eluate. The hydrolysed, deamidated products were freeze-dried for storage.

EXAMPLE 12

Protein Solubility

Soy protein (1.2%, w/v) was homogenized in 0.2M NaCl using an Omni mixer (Ivan Sorvall Inc., Norwalk, Conn.) at 4,000 rpm for 1 min at 25° C. The pH of a 5 mL aliquot was adjusted between 2-10 with either 0.2M NaOH or 0.2M HCl. Then 0.2M NaCl was added to a volume of 6 mL. Protein dispersions were stirred for 45 min and centrifuged at 2000×g for 10 min at 25° C. Protein concentration in both the supernatant and the precipitate (dissolved in 0.01M NaOH) was determined using the bicinchoninic acid method of Smith et al. (1985). The solubility was calculated as follows:

$$\% \text{ Solubility} = \text{Absorbent} \frac{\text{supernatant}}{\text{supernatant} + \text{precipitate}} \times 100$$

EXAMPLE 13

Emulsifying Properties

Emulsifying activity was determined by the method of Pearce and Kinsella, J. Agric. Food Chem., vol. 26, (1978), p. 716. Emulsions were prepared by homogenizing 5 mL of 0.5% soy protein dispersions in 0.1M NaCl, pH 2-9 and 5 mL soy oil aliquots in an Omni mixer at 10,000 rpm for 30 seconds (sec) at 20° C. Aliquots (0.2 mL) of emulsions were diluted to 1/1000 using 0.1% sodium dodecyl sulfate (SDS) and the absorbance at 500 nm was determined. Emulsion stability was determined by the method of Pearce and Kinsella (1978), Ibid., as modified by Kato et al. (1987), Ibid. Three milliliters of soy oil and 10 mL of a 0.1% protein dispersion in 0.1M phosphate buffer, pH 8.0 was homogenized in an Omni Mixer at 12,000 rpm for 1 min at 20° C. Emulsions (0.2 mL) were taken from the bottom of the container after 15 sec from emulsion formation, which was considered the 0 time sample, and in time intervals was up to 20 min, diluted to 1/100 with 0.1% SDS and the absorbance was determined at 500 nm.

EXAMPLE 14

Foaming Properties

Foaming power and foam stability were determined by the conductimetric method of Kato et al., J. Food Sci., vol. 48, (1983b), p. 62. Foams were prepared by sparging 10 mL 0.1% protein solution in 0.1M phosphate buffer, pH 7.5, in a 4×40 cm column with air at constant flow rate of 100 cm$^3$ min$^{-1}$ through a glass sinter, for 15 sec. The conductivity was measured by an electrode cell, connected to a PCMI conductivity meter (Cole-Parmer Instrument Co., Chicago, Ill.) for 5 min. Foaming power was defined as the maximum conductivity of foams produced after aeration. Foam power value was also considered as conductivity at 0 time ($C_0$). The ratio of $C_{0.5}$ to $C_0$ was used to express foaming stability, where $C_{0.5}$ is conductivity after 0.5 min.

Deamidation of Soy Protein and Foaming Properties

Assessment of foaming properties of food proteins are generally based on either bubbling or beating. Although Halling, CRC Crit. Rev. Food Sci. Nutr., vol. 10, (1981), p. 155, reported the structure of foams obtained by the two methods was quite different, Wright and Hemmant J. Sci. Food Agric., vol. 14, (1987), p. 361, observed a good correlation between bubbling and beating. Table 5 presents the foaming power and foaming stability of modified soy proteins. Pretreatment of soy protein substrate prior to deamidation doubled the foaming power but apparently had no effect on foam stability. Changes in foaming properties of control hydrolysates may be a combined effect of limited proteolysis and heat treatment. Soy protein with limited hydrolysis exhibits less stability than unhydrolyzed protein, but the foams are formed more readily [Puski, Cereal Chem., vol. 52, (1975), p. 655]. Kato et al. (1983a), Ibid., reported that heat denaturation of soy globulins increased foaming power and foam stability due to increased surface hydrophobicity. Comparing control hydrolysates to PGase treated hydrolysates, deamidation increased the foaming power of hydrolysates but had no apparent effect on foaming stability (Table 5). Halling (1981) stated that increased solubility and enhanced electrostatic repulsion between adjacent bubbles, may account for the improvement in foaming properties.

Preparation of Enzymatically Deamidated Soy Proteins

This example demonstrates how limited enzymatic deamidation (less than 16% deamidation) can bring about considerable changes in the functional properties of food proteins. In this example, moist heat, limited proteolysis and PGase treatment were combined to produce soy protein at two degrees of hydrolysis and several levels of deamidation, as depicted in the flow chart. The protein content was 57.0% for the freeze-dried water extract of soy flakes and ranged from 52.2 to 53.9 for the lyophilized hydrolysates. PGase treatment had no effect on the degree of hydrolysis as the DH remained constant at 2.0 or 4.0 after deamidation.

TABLE 5

| Foaming Properties of Modified Soy Proteins | | |
|---|---|---|
| Soy Proteins | Foaming Power | Foam Stability |
| Water extract of soy flakes | 257.4 | 0.13 |
| 2 DH heated 15 min, control | 593.0 | 0.13 |
| 6.0% deamidation | 657.4 | 0.14 |
| 2 DH heated 30 min, control | 613.8 | 0.20 |
| 8.2% deamidation | 633.8 | 0.19 |
| 4 DH heated 15 min, control | 627.5 | 0.13 |
| 12.6% deamidation | 643.3 | 0.12 |
| 4 DH heated 30 min, control | 642.0 | 0.12 |
| 16.0% deamidation | 747.5 | 0.12 |

The extent of deamidation was 6.0% and 8.2% at 2.0 DH and 12.8% and 16.0% at 4.0 DH when the hydrolysates were heated for 15 and 30 min, respectively. Since heat treatment and proteolysis of soy proteins were used as a means to achieve significant deamidation, heat-treated soy protein hydrolysates were used as controls. Therefore, changes in protein functional properties were due only to deamidation and not heat treatment and proteolysis.

Deamidation and Protein Solubility

Figure 7A:
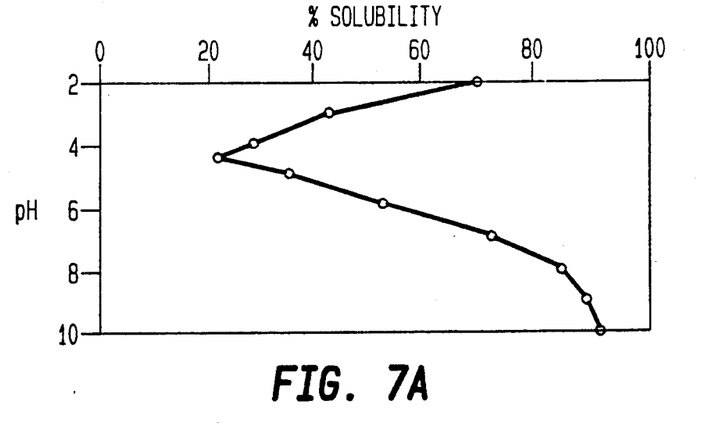
Figure 7B:
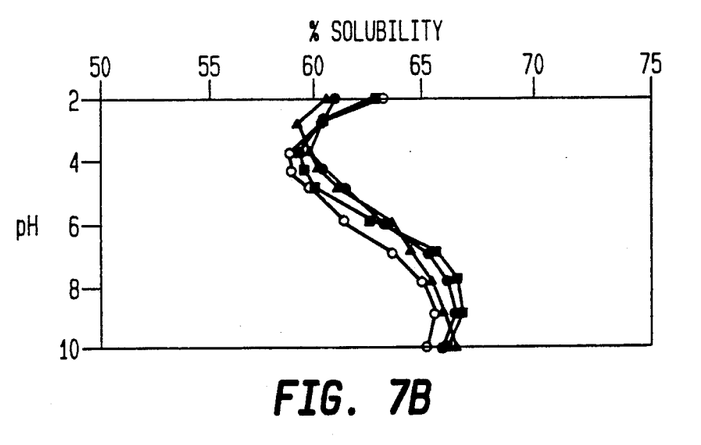
Figure 7C:
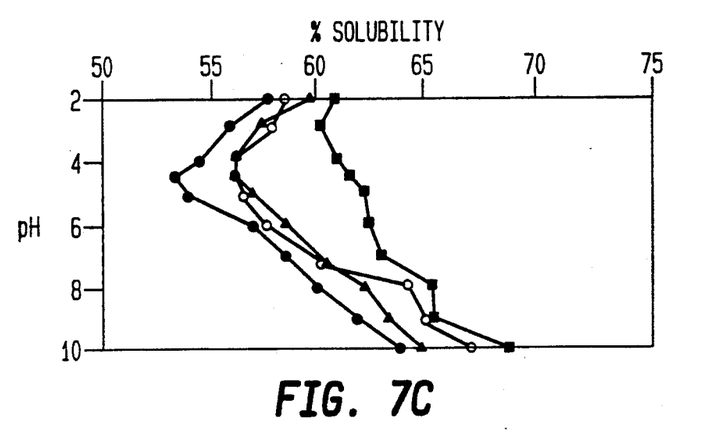

The solubilities of the native soy protein, heat-treated hydrolysates and the deamidated, heat-treated hydrolysates in 0.2M sodium chloride, as a function of pH are presented in FIG. 7. The pH-solubility of deamidated, soy protein hydrolysates at 2.0 DH was similar to the hydrolysed controls, but the pH-solubility of deamidated, soy protein hydrolysates at 4.0 DH was considerably greater than their respective controls (FIG. 7). The solubility of deamidated, soy protein hydrolysates increased in the isoelectric pH range of 4 and 5 and in the pH regions of 4-7 as well as under alkaline conditions, as a result of deamidation. Deamidation increased the negative charge of the hydrolysates and might disrupt hydrophobic and hydrogen bonds.

Emulsification Properties of Deamidated Soy Proteins

Figure 8A:
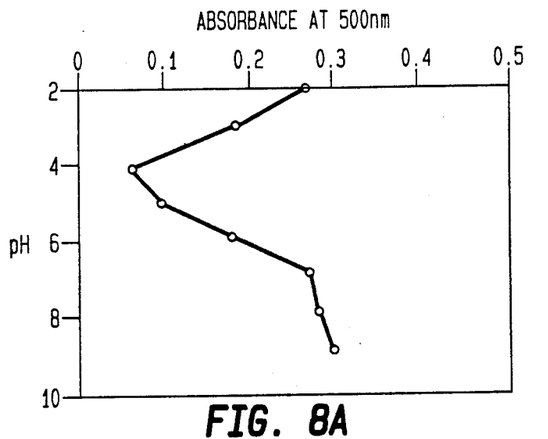
Figure 8B:
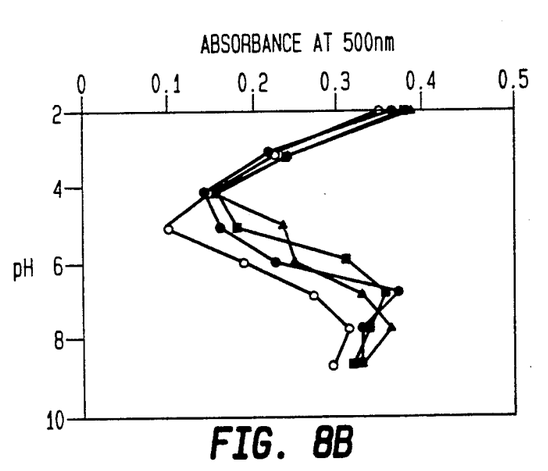
Figure 8C:
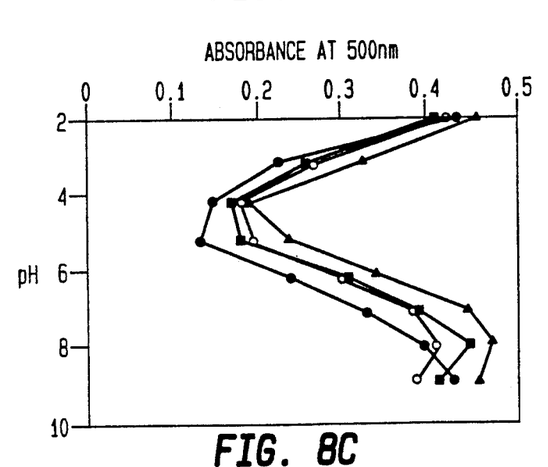

Emulsifying activity, the ability of protein to serve as emulsifying agent in the formation of a stable emulsion, is expressed as the absorbance of diluted emulsions at 500 nm (Pierce and Kinsella, 1978, Ibid.). FIG. 8 presents the emulsifying activity of the unmodified, heat-treated hydrolysates and the deamidated, heat-treated hydrolysates in the pH range of 2-9. Protein hydrolysates exhibited greater emulsifying activity than intact protein. Limited hydrolysis of soy proteins increases emulsifying capacity (Puski, 1975, Ibid.). Emulsifying activity of heat-treated hydrolysates increased with the increase in the rate of deamidation, especially in the acidic pH region. The profiles of emulsifying activity in the pH range of 2-9 of deamidated hydrolysates resembled the protein solubility curves (FIG. 7), suggesting that the solubility of the protein is a prerequisite for emulsifying activity. Increased solubility of modified soy protein facilitates the formation of a stronger interfacial film [Huang and Kinsella, J. Food Sci., vol. 52, (1987), p. 1684].

The ability of discrete emulsion droplets to remain dispersed without separating is defined as emulsion stability. The time dependent changes in turbidity of diluted emulsions produced of controls and deamidated proteins are given in FIG. 9. Turbidity declined for 1-4 min and stabilized for the remainder of the assay. The emulsion stability of soy protein dispersion decreased upon proteolysis. This effect of proteolysis on emulsion stability has been previously reported [Puski (1975), Ibid.].

Figure 9A:
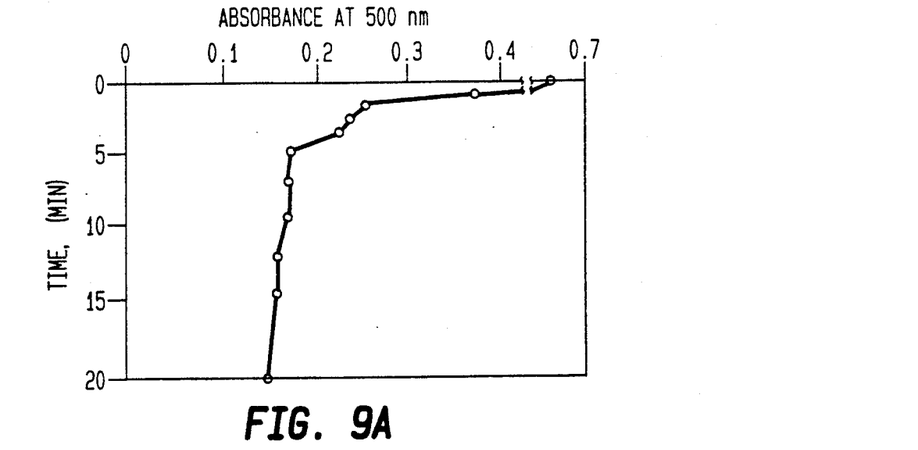
Figure 9B:
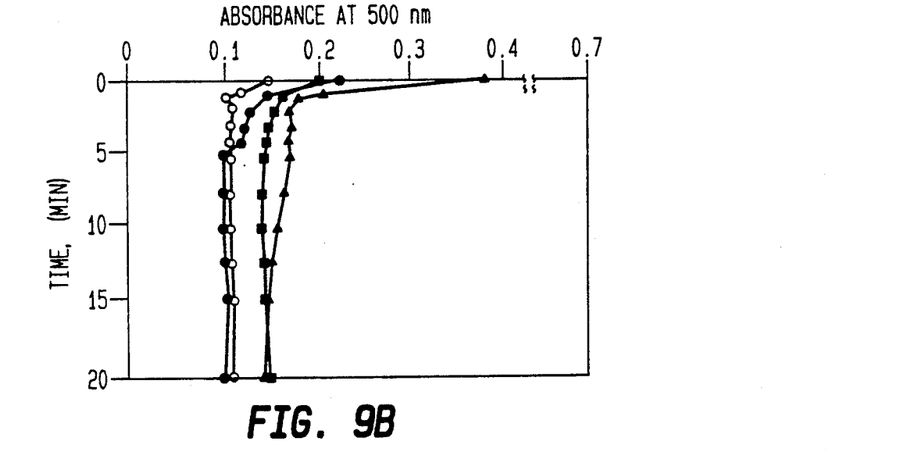
Figure 9C:
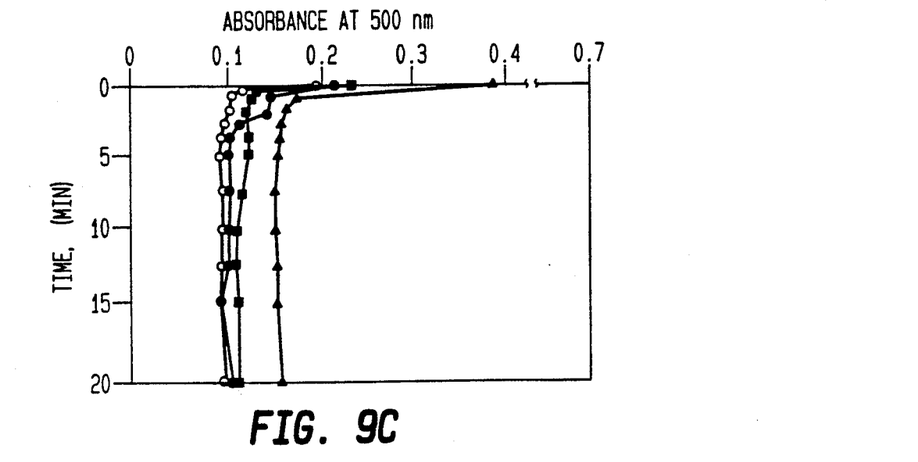

Emulsion stability of the deamidated, hydrolysed proteins was substantially improved over the 2.0 and 4.0 DH controls, particularly in the hydrolysate deamidated to 16%. The increase in emulsion stability resulting from deamidation may be dependent on the increase in the number of negative charge (Halling, 1981, Ibid), the surface hydrophobicity and the flexibility of the protein brought about by deamidation [Kato et al. (1987), Ibid.]. Kato et al. (1987), Ibid., reported also that deamidation improved emulsifying activity and emulsion stability.

I claim:
1. A method of treating food proteins to enhance solubility, emulsifying and foaming properties consisting essentially of:
   a) denaturing a food protein to form a denatured protein;
   b) hydrolyzing said denatured protein; and
   c) deamidating by treatment with peptidoglutaminase.
2. The method of claim 1 wherein the denaturing step is accomplished by heating for a predetermined period of time.
3. The method of claim 2 wherein a temperature is selected at about 100° C. for a predetermined period of time of about 15 min.
4. The method of claim 1 wherein hydrolyzing said protein is accomplished by treatment with an alkaline protease and monitoring the pH.
5. A method of treating food protein to enhance solubility, emulsifying and foaming properties consisting essentially of:
   a) obtaining a soluble protein extract;
   b) heating said protein extract at about 100° C. for about 15 min to form a denatured protein;
   c) treating said denatured protein with a protease to form a hydrolyzed protein;
   d) heating said hydrolyzed protein at about 100° C. for from about 15 to about 30 min; and
   e) treating said hydrolyzed protein with peptidoglutaminase.

* * * * *